United States Patent [19]
Hunziker

[11] Patent Number: 5,853,746
[45] Date of Patent: Dec. 29, 1998

[54] METHODS AND COMPOSITIONS FOR THE TREATMENT AND REPAIR OF DEFECTS OR LESIONS IN CARTILAGE OR BONE USING FUNCTIONAL BARRIER

[75] Inventor: Ernst B. Hunziker, Riedholz, Switzerland

[73] Assignee: Robert Francis Shaw, Sausalito, Calif.

[21] Appl. No.: 672,618

[22] Filed: Jun. 28, 1996

Related U.S. Application Data

[63] Continuation-in-part of Ser. No. 524,034, Sep. 6, 1995, abandoned, which is a continuation of Ser. No. 338,126, Nov. 1, 1994, abandoned, which is a continuation of Ser. No. 979,904, Nov. 23, 1992, Pat. No. 5,368,858, which is a division of Ser. No. 648,274, Jan. 31, 1991, Pat. No. 5,206,023.

[51] Int. Cl.$^6$ ............................ A61F 2/28; A61K 9/127; A61K 9/50
[52] U.S. Cl. .......................... 424/426; 424/450; 424/499; 514/944; 514/953; 514/965
[58] Field of Search ..................... 424/423, 424, 424/425, 426, 450, 484, 489, 499; 514/944, 953, 965

[56] References Cited

U.S. PATENT DOCUMENTS

| | | |
|---|---|---|
| 4,563,350 | 1/1986 | Nathan et al. . |
| 4,609,551 | 9/1986 | Caplan et al. . |
| 4,642,120 | 2/1987 | Nevo et al. . |
| 4,846,835 | 7/1989 | Grande . |
| 4,904,259 | 2/1990 | Italy . |
| 4,950,483 | 8/1990 | Ksander et al. . |
| 4,994,443 | 2/1991 | Folkman et al. . |
| 4,996,159 | 2/1991 | Glaser . |
| 5,001,116 | 3/1991 | Folkman et al. . |
| 5,041,138 | 8/1991 | Vicanti et al. . |
| 5,206,023 | 4/1993 | Hunziker . |
| 5,268,384 | 12/1993 | Galardy . |
| 5,270,300 | 12/1993 | Hunziker . |
| 5,286,716 | 2/1994 | Risau . |
| 5,306,311 | 4/1994 | Stone et al. . |
| 5,368,051 | 11/1994 | Dunn et al. . |
| 5,368,858 | 11/1994 | Hunziker . |

FOREIGN PATENT DOCUMENTS

| | | |
|---|---|---|
| 569541 | 5/1995 | European Pat. Off. . |
| WO 91/11193 | 8/1991 | WIPO . |
| WO 92/13565 | 8/1992 | WIPO . |
| WO 93/04710 | 3/1993 | WIPO . |
| WO 95/13830 | 5/1995 | WIPO . |

OTHER PUBLICATIONS

Coomber, "Suramin Inhibits C6 Glioma–Induced Angiogenesis In Vitro," *J. Cell. Biochem.*, 58, pp. 199–207 (1995).

Dahlin et al., "Healing of Bone Defects by Guided Tissue Regeneration," *Plastic & Reconstructive Surgery*, 81(5), pp. 672–676 (1988).

Davidson et al. Accelerated Wound Repair, Cell Proliferation, and Collagen Accumulation Are Produced By A Cartilage Derived Growth Factor, 100, *J. Cell Bio.*, pp. 1219–1227 (1985).

Diaz–Flores et al, "Angiogenesis: An Update," *Histology & Histopathology*, 9(4), pp. 807–843 (1994).

Dijke & Iwat, "Growth Factors For Wound Healing," *Biotech.*, 7, pp. 793–798 (1989).

Farso et al., "Guided Tissue Regeneration In Long Bone Defects In Rabbits," *Acta Orthop.*, 63, pp. 66–69 (1992).

Folkman & Klagshrun, "Angiogenic Factors," *Science*, 235, pp. 442–444 (1987).

Ingber et al., "Synthetic Analogues Of Fumagillin That Inhibit Angiogenesis And Suppress Tumor Growth," *Nature*, 348, pp. 555–557 (1990).

Karring et al., "Guided Tissue Regeneration Using Biodegradable Membranes Of Polylactic Acid Or Polyurethane," *J. Clin. Periodontol.*, 19, pp. 633–640 (1992).

Kuettner et al., "Morphological Studies On The Resistance Of Cartilage To Invasion By Osteosarcoma cells in Vitro And In Vivo," *Cancer Research*, 36, pp. 277–287 (1975).

Langer, "Drug Delivery Systems For Angiogenesis Simulators & Inhibitors," *J. Cell. Biochem.*, 16A, p. 39, abstract CA 023 (1992).

Moses, "A Cartilage–derived Inhibitor Of Neovascularization And Metalloproteinases," *Clinical & Expt'l Rheumatology*, 11(Supp. 8), pp. S67–S69 (1993).

Moses & Langer, "A Metalloproteinase Inhibitor As An Inhibitor Of Neovascularization," *J. Cell. Biochem.*, 47, pp. 230–235 (1991).

Moses et al., "Isolation And Characterization Of An Inhibitor Of Neovascularization From Scapular Chondrocytes," *J. Cell Bio.*, 1992 (pp. 475–482(1992).

(List continued on next page.)

*Primary Examiner*—Carlos A. Azpuru
*Attorney, Agent, or Firm*—Fish & Neave; Jane A. Massaro; Mark J. Rosen

[57] ABSTRACT

Methods and compositions are provided for the treatment and repair of defects in the cartilage or bone of humans and other animals as in full-thickness defects in joints. To induce cartilage formation, a defect in cartilage is filled with a matrix having pores sufficiently large to allow cartilage repair cells to populate the matrix. The matrix contains an anti-angiogenic agent that serves as a functional barrier to prevent vascularization and bone growth into the cartilage area. The matrix filling the defect in cartilage may also contain a proliferation agent and a chemotactic agent, and a transforming factor in an appropriate delivery system. A functional barrier between the bone and cartilage areas of a full-thickness defect may also be created by heat-treating the areas of bleeding to form a transient tissue barrier which prevents blood vessels and associated cells from penetrating from the bone area into the cartilage area. If desired, the bone portion of the full-thickness defect may be filled with a matrix having pores large enough to allow cells to populate the matrix and to form blood vessels. The matrix filling the bone defect may contain an angiogenic factor and an osteogenic factor in an appropriate delivery system. Methods and compositions are also provided for assisted bone and connective tissue regeneration for dental and other applications.

30 Claims, No Drawings

OTHER PUBLICATIONS

Moses et al., "Identification Of An Inhibitor of Neovascularization From Cartilage," *Science*, 248, 1408–10 (1990).

"Neovascularisation And Its Role In The Osteoarthritic Process," *Annals of Rheumatic Diseases*, 47, 881–85 (1988).

Peacock et al., "A Novel Angiogenesis Inhibitor Suppresses Rat Adjuvant Arthritis," *Cellular Immunology*, 160(2), pp. 178–184 (1995).

Pepper, "Chondrocytes Inhibit Endothelial Spout Formation In Vitro: Evidence For Involvement Of A Transforming Growth Factor–Beta," *Journal of Cellular Physiology*, 146, pp. 170–179 (1991).

Robert & Frank, "Periodontal Guided Tissue Regeneration With A New Resorbable Polylactic Acid Membrane," *J. Periodontol.* 65, 441–22 (1994).

Rogachefsky et al., "Treatment Of Canine Osteoarthritis With Insulin–like Growth Factor–1 (IGF–1) and Sodium Pentosan Polysulfate," *Osteoarthritis and Cartilage*, 1, pp. 105–114 (1993).

Sorgente et al., "The Resistance Of Certain Tissues To Invasion: Evidence For Extrasctable Factors In Cartilage Which Inhibit Invasion By Vascularized Mesenchyme," *Lab. Investig.*, 32(2), pp. 217–222 (1975).

METHODS AND COMPOSITIONS FOR THE TREATMENT AND REPAIR OF DEFECTS OR LESIONS IN CARTILAGE OR BONE USING FUNCTIONAL BARRIER

This is a continuation in part of U.S. application Ser. No. 08/524,034, filed Sep. 6, 1995, now abandoned, which is a continuation of prior U.S. application Ser. No. 08/333,156, filed Nov. 1, 1994, now abandoned, which is a continuation of prior U.S. application Ser. No. 07/979,904, filed Nov. 23, 1992, now U.S. Pat. No. 5,368,858 which is a divisional application of prior U.S. application Ser. No. 07/648,274, filed Jan. 31, 1991, now U.S. Pat. No. 5,206,023.

TECHNICAL FIELD OF THE INVENTION

This invention relates to the treatment and repair of defects or lesions in cartilage and full-thickness defects or lesions in cartilage and bone. More specifically, this invention relates to methods for treating defects or lesions (used interchangeably herein) in cartilage and bone and to cartilage repair compositions comprising a matrix containing an anti-angiogenic agent as a "functional barrier" to prevent ingrowth of blood vessels from the underlying bone tissue into the new cartilage tissue. The cartilage repair composition may also contain one or more proliferating agents and a transforming factor to promote proliferation and transformation of cartilage repair cells to form new stable cartilage tissue. Bone repair compositions comprising a matrix containing an angiogenic factor to stimulate blood vessel formation and an osteogenic factor to stimulate formation of bone may also be used to treat the bone portion of full-thickness defects. The compositions and methods of this invention are particularly useful in the treatment of full-thickness defects found in severe osteoarthritis, and in other diseases and traumas that produce cartilage and bone injury. Other compositions and methods of this invention, using other anti-tissue factors as functional barriers, are useful in treating other injuries and defects such as in periodontal disease, where it is desired to inhibit or delay growth of certain tissue.

BACKGROUND ART

Joints are one of the common ways bones in the skeleton are connected. The ends of normal articulated bones are covered by articular cartilage tissue, which permits practically frictionless movement of the bones with respect to one another [L. Weiss, ed., *Cell and Tissue Biology* (Munchen: Urban and Schwarzenburg, 1988) p. 247].

Articular cartilage is characterized by a particular structural organization. It consists of specialized cells (chondrocytes) embedded in an intercellular material (often referred to in the literature as the "cartilage matrix") which is rich in proteoglycans, collagen fibrils of predominantly type II, other proteins, and water [Buckwalter et al., "Articular Cartilage: Injury and Repair," in *Injury and Repair of the Musculoskeletal Soft Tissues* (Park Ridge, Ill.: American Academy of Orthopaedic Surgeons Symposium, 1987) p. 465]. Cartilage tissue is neither innervated nor penetrated by the vascular or lymphatic systems. However, in the mature joint of adults, the underlying subchondral bone tissue, which forms a narrow, continuous plate between the bone tissue and the cartilage, is innervated and vascularized. Beneath this bone plate, the bone tissue forms trabeculae, containing the marrow. In immature joints, articular cartilage is underlined by only primary bone trabeculae. A portion of the meniscal tissue in joints also consists of cartilage whose make-up is similar to articular cartilage [Beaupre, A. et al., *Clin. Orthop. Rel. Res.*, pp. 72–76 (1986)].

Two types of defects are recognized in articular surfaces, i.e., full-thickness defects and superficial defects. These defects differ not only in the extent of physical damage to the cartilage, but also in the nature of the repair response each type of lesion can elicit.

Full-thickness defects of an articular surface include damage to the hyaline cartilage, the calcified cartilage layer and the subchondral bone tissue with its blood vessels and bone marrow. The damage to the bone tissue may range from a fissure or crack to an enlarged gap in the bone tissue. Full-thickness defects can cause severe pain since the bone plate contains sensory nerve endings. Such defects generally arise from severe trauma or during the late stages of degenerative joint disease, such as osteoarthritis. Full-thickness defects may, on occasion, lead to bleeding and the induction of a repair reaction from the subchondral bone [Buckwalter et al., "Articular Cartilage: Composition, Structure, Response to Injury, and Methods of Facilitating Repair," in *Articular Cartilage and Knee Joint Function: Basic Science and Arthroscopy* (New York: Raven Press, 1990) pp. 19–56]. The repair tissue formed is a vascularized fibrous type of cartilage with insufficient biomechanical properties, and does not persist on a long-term basis [Buckwalter et al. (1990), supra].

Superficial defects in the articular cartilage tissue are restricted to the cartilage tissue itself Such defects are notorious because they do not heal and show no propensity for repair reactions.

Superficial defects may appear as fissures, divots, or clefts in the surface of the cartilage, or they may have a "crab-meat" appearance in the affected tissue. They contain no bleeding vessels (blood spots) such as are seen in full-thickness defects. Superficial defects may have no known cause, but often they are the result of mechanical derangements which lead to a wearing down of the cartilaginous tissue. Mechanical derangements may be caused by trauma to the joint, e.g., a displacement of torn meniscus tissue into the joint, meniscectomy, a laxation of the joint by a torn ligament, malalignment of joints, or bone fracture, or by hereditary diseases. Superficial defects are also characteristic of early stages of degenerative joint diseases, such as osteoarthritis. Since the cartilage tissue is not innervated [*Ham's Histology* (9th ed.) (Philadelphia: J. B. Lippincott Co. 1987), pp. 266–272] or vascularized, superficial defects are not painful. However, although painless, superficial defects do not heal and often degenerate into full-thickness defects.

It is generally believed that because articular cartilage lacks a vasculature, damaged cartilage tissue does not receive sufficient or proper stimuli to elicit a repair response [Webber et al., "Intrinsic Repair Capabilities of Rabbit Meniscal Fibrocartilage: A Cell Culture Model", (30th Ann. Orthop. Res. Soc., Atlanta, Feb. 1984); Webber et al., *J. Orthop. Res.*, 3, pp. 36–42 (1985)]. It is theorized that the chondrocytes in the cartilaginous tissue are normally not exposed to sufficient amounts of repair-stimulating agents such as growth factors and fibrin clots typically present in damaged vascularized tissue.

One approach that has been used to expose damaged cartilage tissue to repair stimuli involves drilling or scraping through the cartilage into the subchondral bone to cause bleeding [Buckwalter et al. (1990), supra]. Unfortunately, the repair response of the tissue to such surgical trauma is usually comparable to that observed to take place naturally in full-thickness defects that cause bleeding, viz., formation of a fibrous type of cartilage which exhibits insufficient biomechanical properties and which does not persist on a long-term basis [Buckwalter et al. (1990), supra].

A variety of growth factors have been isolated and are now available for research and biomedical applications [see e.g., Rizzino, A., *Dev. Biol.*, 130, pp. 411–422 (1988)]. Some of these growth factors, such as transforming growth factor beta (TGF-β), have been reported to promote formation of cartilage-specific molecules, such as type II collagen and cartilage-specific proteoglycans, in embryonic rat mesenchymal cells in vitro [e.g., Seyedin et al., *Proc. Natl. Acad. Sci. USA*, 82, pp. 2267–71 (1985); Seyedin et al., *J. Biol. Chem.*, 261, pp. 5693–95 (1986); Seyedin et al., *J. Biol. Chem.*, 262, pp. 1946–1949 (1987)].

Furthermore, a number of protein factors have been identified that apparently stimulate formation of bone. Such osteogenic factors include bone morphogenetic proteins, osteogenin, bone osteogenic protein (BOP), TGF-βs, and recombinant bone inducing proteins.

Millions of patients have been diagnosed as having osteoarthritis, i.e., as having degenerating defects or lesions in their articular cartilage. Nevertheless, despite claims of various methods to elicit a repair response in damaged cartilage, none of these treatments has received substantial application [Buckwalter et al. (1990), supra; Knutson et al., *J. Bone and Joint Surg.*, 68-B, p. 795 (1986); Knutson et al., *J. Bone and Joint Surg.*, 67-B, p. 47 (1985); Knutson et al., *Clin. Orthop.*, 191, p. 202 (1984); Marquet, *Clin. Orthop.*, 146, p. 102 (1980)]. And such treatments have generally provided only temporary relief Systemic use of "chondroprotective agents" has also been purported to arrest the progression of osteoarthritis and to induce relief of pain. However, such agents have not been shown to promote repair of lesions or defects in cartilage tissue.

To date, treatment of patients suffering from osteoarthritis has been directed largely to symptomatic relief through the use of analgesics and anti-inflammatory agents. Without a treatment that will elicit repair of superficial defects in articular cartilage, the cartilage frequently wears down to the subchondral bone plate. At this phase of the disease, i.e., severe osteoarthritis, the unremitting nature of the pain and the significant compromise of function often dictates that the entire joint be excised and replaced with an artificial joint of metal and/or plastic. Some one-half million procedures comprising joint resection and replacement with an artificial joint are currently performed on knees and hips each year. [See e.g., Graves, E. J., "1988 Summary; National Hospital Discharge Survey", *Advanced Data From Vital and Health Statistics*, 85, pp. 1–12 (Jun. 19, 1990)].

There is, therefore, a need for a reliable treatment for cartilage tissue in superficial cartilage defects and for cartilage and bone tissue in full thickness defects, e.g., as found in cases of severe osteoarthritis.

In addition to cartilage tissue defects, there are other defects for which improved treatment is required. One area in which improved treatment methods are needed is in periodontal repair and regeneration. Currently, physical, usually membrane-based, barriers are used to prevent unwanted tissue ingrowth between compartments in, for example, cases of severe paradontitis. [See, e.g., Robert, P. M., and Frank, R. M., "Peridontal guided tissue regeneration with a new resorbable polyactic acid membrane," *J. Periodonto*, 65.5, pp. 414–422 (1994).]. Physical membranes are also used in orthopedic guided tissue regenerations. [See, e.g., Farso, R. et al., "Guided tissue regeneration in long bone defects in rabbits," *Acta Orthop*, 63, pp. 66–69 (1992)]. However, these procedures are not desirable because the membranes are usually not biodegradable and a second surgical intervention is thus necessary. In addition, the physical membranes that are biodegradable are often associated with long-lasting adverse effects, including inflammation, and chronic foreign body reaction because the degradation products of the membrane lead to local chronic inflammatory responses, and in association with this, lead to inhibition of surrounding tissue differentiation processes. There is therefore a need for an improved method of assisting in bone regeneration for periodontal and orthopedic repair.

SUMMARY OF THE INVENTION

The present invention solves the problems referred to above by providing effective therapeutic methods and compositions to induce the repair of lesions in cartilage or bone of humans and other animals. Use of the methods and compositions of this invention also promote the healing of traumatic lesions and forms of osteoarthritis which would otherwise lead to loss of effective joint function leading to probable resection and replacement of the joint.

In general outline, the methods and compositions of this invention for treating superficial cartilage defects or the cartilage portion of full-thickness defects comprise filling the cartilage portion of the defect with a cartilage repair matrix containing an anti-angiogenic agent for inhibiting vascular ingrowth such as anti-invasive factor, metalloprotease inhibitor or antibodies against angiogenesis-inducing factors. The cartilage repair matrix will be incorporated into the animal tissue and is generally biodegradable; it may also contain a proliferation agent and a transforming factor. The cartilage repair matrices of this invention are particularly useful for treating full-thickness defects and apparent superficial cartilage defects where there is a possibility of a crack or fissure in the bone below.

In another embodiment, the methods of this invention comprise heat-treating the areas in a full thickness defect where bleeding has occurred to create a transient tissue barrier and then filling the defect with a cartilage repair matrix. In this embodiment, the anti-angiogenic agent may be omitted from the matrix.

The methods of this invention for repairing full-thickness defects in joints also comprise, where necessary or desirable due to extensive bone injury, filling the defect in the bone portion of a full-thickness defect up to the level of the bone-cartilage interface with a matrix that will be incorporated into the animal tissue and is generally biodegradable. The bone repair matrix may contain angiogenic and osteogenic factors. The remaining cartilage portion of the defect is filled to the top of the cartilage surface with a cartilage repair matrix containing an anti-angiogenic agent for inhibiting vascular ingrowth. The cartilage repair matrix may also contain a proliferation agent and a transforming factor.

Treatment of superficial and full-thickness defects can be effected during arthroscopic, open surgical or percutaneous procedures using the methods of this invention. According to certain methods of this invention, after identification of a full thickness defect, the defect is treated by the steps of (1) filling the bone portion of the defect with a composition comprising a matrix containing an angiogenic factor and an osteogenic factor packaged in an appropriate delivery system, e.g., liposomes; and (2) filling the cartilage portion of the defect with a composition comprising a matrix, preferably biodegradable, containing an anti-angiogenic agent and a transforming factor which is packaged in an appropriate delivery system. In this second step, the matrix may be bonded to the surface of the cartilage portion of the full-thickness defect, for example, by using an adhesion-promoting factor, such as transglutaminase.

Treatment of periodontal disease may be also aided with the methods and compositions of this invention. For example, in the treatment of disease such as paradontitis, in which the periodontal ligament recesses and toothnecks are exposed, the regeneration of periodontal connective tissue can be aided by filling the periodontal connective tissue space with a matrix containing one or more factors to stimulate periodontal tissue formation and one or more inhibitors of epithelium formation.

Bone regeneration following loss of teeth can also be aided by the methods and compositions of this invention. In particular, the bone of the maxillar or mandibular ridge can be built up by filling the defect area with a bone-inducing biodegradable matrix containing angiogenic and osteogenic factors and inhibitors for migration and/or proliferation and/or differentiation of connective tissue cells to assist in the re-growth of bone tissue. Within the periodontal connective tissue compartment a biodegradable matrix containing one or more factors to stimulate periodontal tissue formation can be used.

Methods and compositions of this invention can also be used to prevent periarticular calcification and ossification following, e.g., joint replacement, and to prevent bone growth into cartilagenous growth plates in young animals and children with distal end bone fractures. In particular, the periarticular connective tissue space or cartilagenous growth space can be filled with a matrix containing an anti-angiogenic factor or anti-bone factors to prevent calcification and bony tissue formation.

DETAILED DESCRIPTION OF INVENTION

In order that the invention may be more fully understood, the following detailed description is provided. In the description the following terms are used.

Angiogenic Factor—as used herein, refers to any peptide, polypeptide, protein or any other compound or composition which induces or stimulates the formation of blood vessels and associated cells (such as endothelial, perivascular, mesenchymal and smooth muscle cells) and blood vessel-associated basement membranes. In vivo and in vitro assays for angiogenic factors are well-known in the art [e.g., Gimbrone, M. A., et al., *J. Natl. Cancer Inst.*, 52, pp. 413–419 (1974); Klagsbrun, M. et al., *Cancer Res.*, 36, pp. 110–113 (1976); Gross et al., *Proc. Natl. Acad. Sci. (USA)*, 80, pp. 2623–2627 (1983); Gospodarowicz et al., *Proc. Natl. Acad. Sci. (USA)*, 73, pp. 4120–4124 (1976); Folkman et al., *Proc. Natl. Acad. Sci. (USA)*, 76, pp. 5217–5221 (1979); Zetter, B. R., *Nature (London)*, 285, pp. 41–43 (1980); Azizkhan, R. G. et al., *J. Exp. Med.*, 152, pp. 931–944 (1980)].

Anti-Angiogenic Agent—as used herein, refers to any compound or composition with biological activity that prevents ingrowth of blood vessels from the underlying bone tissue into the cartilage tissue, such as anti-invasive factors, cartilage-derived angiogenesis inhibitors, angiostatin, metalloprotease inhibitors, antibodies against angiogenesis-inducing factors (including bFGF and endothelial cell stimulating angiogenic factor (ESAF)), Suramin (Germanin®, Bayer Co., Germany), fumagillin, fumagillin analogues and AGM-1470 [Peacock, D. J. et al., *Cellular Immunology*, 160, pp. 178–84 (1995)]. In vivo and in vitro assays to determine anti-angiogenic agents are well-known in the art [e.g., Moses, M. A., *Clinical & Exptl. Rheumatology*, 11(Suppl. 8), pp. 567–69 (1993); Moses, M. A. et al., *J. Cell Bio.*, 119(2), pp. 475–82 (1992); Moses, M. A. et al., *Science*, 248, pp. 1408–10 (1990); Ingber, D. et al., *Nature*, 348(6), pp. 555–57 (1990)].

Anti-Tissue Factors—as used herein, refers to any compound or composition with biological activity that selectively prevents unwanted growth of particular tissues. For example, anti-epithelial factors to selectively inhibit epithelium formation include anti-epithelial antibodies, vitamin A inhibitors, anti-retinol, anti-basement membrane antibodies, epidermal growth factor inhibitors, matrices enriched with fibronectin, and any other factors that inhibit epithelial cell proliferation, growth or differentiation or epithelium formation. [See, e.g., Adams, J. C. and Watt, F. M., "Fibronectin inhibits the terminal differentiation of human keratinocytes", *Nature*, 340, pp.307–09 (1989).] Anti-connective tissue factors to selectively inhibit connective tissue formation include anti-connective tissue antibodies, antibodies against connective tissue-specific growth factors, antibodies against mesenchymal cell surface proteins, and factors inhibiting mesenchymal cell proliferation. Anti-bone factors to selectively inhibit bone tissue formation include anti-angiogenic factors, and monoclonal or polyclonal antibodies, or combinations thereof, against members of the TGF-β superfamily.

Arthroscopy—as used herein, refers to the use of an arthroscope to examine or perform surgery on a joint.

Bone—as used herein, refers to a calcified connective tissue primarily comprising a network of deposited calcium and phosphate in the form of hydroxyapatite, collagen (predominantly type I collagen) and bone cells, such as osteoblasts and osteoclasts.

Bone Repair Cell—as used herein, refers to a cell which, when exposed to appropriate stimuli, will differentiate and be transformed into a bone cell, such as an osteoblast or an osteocyte, which forms bone. Bone repair cells include perivascular cells, mesenchymal cells, fibroblasts, fibroblast-like cells and dedifferentiated chondrocytes.

Cartilage—as used herein, refers to a type of connective tissue that contains chondrocytes embedded in an intercellular material (often referred to as the "cartilage matrix") comprising fibrils of collagen (predominantly type II collagen along with other minor types, e.g., types IX and XI), various proteoglycans (e.g., chondroitinsulfate-, keratansulfate-, and dermatansulfate proteoglycans), other proteins, and water. Cartilage as used herein includes articular and meniscal cartilage. Articular cartilage covers the surfaces of the portions of bones in joints and allows movement in joints without direct bone-to-bone contact, and thereby prevents wearing down and damage to apposing bone surfaces. Most normal healthy articular cartilage is also described as "hyaline", i.e., having a characteristic frosted glass appearance. Meniscal cartilage is usually found in joints which are exposed to concussion as well as movement. Such locations of meniscal cartilage include the temporo-mandibular, sterno-clavicular, acromio-clavicular, wrist and knee joints [Gray's Anatomy (New York: Bounty Books, 1977)].

Cartilage Repair Cell—as used herein, refers to a cell which, when exposed to appropriate stimuli, will differentiate and be transformed into a chondrocyte. Cartilage repair cells include mesenchymal cells, fibroblasts, fibroblast-like cells, macrophages and dedifferentiated chondrocytes.

Cell Adhesion Promoting Factor—as used herein, refers to any compound or composition, including fibronectin and other peptides as small as tetrapeptides which comprise the tripeptide Arg-Gly-Asp, which mediates the adhesion of cells to extracellular material [Ruoslathi et al., Cell, 44, pp. 517–518 (1986)].

Chemotactic Agent—as used herein, refers to any compound or composition, including peptides, proteins, glycoproteins and glycosaminoglycan chains, which is capable of attracting cells in standard in vitro chemotactic assays [e.g., Wahl et al., Proc. Natl. Acad. Sci. USA, 84, pp. 5788–92 (1987), Postlewaite et al., J. Exp. Med., 165, pp. 251–56 (1987); Moore et al., Int. J. Tiss. Reac., XI pp. 301–07 (1989)].

Chondrocytes—as used herein, refers to cells which are capable of producing components of cartilage tissue, e.g., type II cartilaginous fibrils and fibers and proteoglycans.

Fibroblast growth factor (FGF)—any member of the family of FGF polypeptides [Gimenez-Gallego et al., Biochem. Biophys. Res. Commun., 135, pp. 541–548 (1986); Thomas et al., Trends Biochem. Sci., 11, pp. 81–84 (1986)] or derivatives thereof, obtained from natural, synthetic or recombinant sources, which exhibits the ability to stimulate DNA synthesis and cell division in vitro [for assays see, e.g., Gimenez-Gallego et al., 1986, supra; Canalis et al., J. Clin. Invest., 81, pp. 1572–1577 (1988)] of a variety of cells, including primary fibroblasts, chondrocytes, vascular and corneal endothelial cells, osteoblasts, myoblasts, smooth muscle and glial cells [Thomas et al., 1986, supra]. FGFs may be classified as acidic (aFGF) or basic (bFGF) FGF, depending on their isoelectric points (pI).

Matrix—as used herein, refers to a porous composite, solid or semi-solid substance having pores or spaces sufficiently large to allow cells to populate the matrix. The term matrix includes matrix-forming materials, i.e., materials which can form matrices within a defect site in cartilage or bone. Matrix-forming materials may require addition of a polymerizing agent to form a matrix, such as adding thrombin to a solution containing fibrinogen to form a fibrin matrix. Other matrix materials include collagen, combinations of collagen and fibrin, agarose (e.g., Sepharose®), and gelatin. Calcium phosphates, such as tricalcium phosphate, hydroxyapatite or other calcium salts that form solid matrices may be used alone or in combination with other matrix materials in treating defects in bones.

Membrane—as used herein, refers to any material which can be placed between the bone defect portion and the cartilage defect portion of a full thickness defect and which prevents cell migration and blood vessel infiltration from the bone defect portion into the cartilage defect portion of the full thickness defect. The membranes used in the methods and compositions of this invention for the repair of full thickness defects are preferably biodegradable.

Osteogenic Factor—as used herein, refers to any peptide, polypeptide, protein or any other compound or composition which induces or stimulates the formation of bone. The osteogenic factor induces differentiation of bone repair cells into bone cells, such as osteoblasts or osteocytes. This process may be reached via an intermediary state of cartilage tissue. The bone tissue formed from bone cells will contain bone specific substances such as type I collagen fibrils, hydroxyapatite mineral and various glycoproteins and small amounts of bone proteoglycans.

Proliferation (mitogenic) Agent—as used herein, refers to any compound or composition, including peptides, proteins, and glycoproteins, which is capable of stimulating proliferation of cells in vitro. In vitro assays to determine the proliferation (mitogenic) activity of peptides, polypeptides and other compounds are well-known in the art [see, e.g., Canalis et al., J. Clin. Invest., pp. 1572–77 (1988); Gimenez-Gallego et al., Biochem. Biophys. Res. Commun., 135, pp. 541–548 (1986); Rizzino, "Soft Agar Growth Assays for Transforming Growth Factors and Mitogenic Peptides", in Methods Enzymol., 146A (New York: Academic Press, 1987), pp. 341–52, Dickson et al., "Assay of Mitogen-Induced Effects on Cellular Incorporation of Precursors for Scavengers, de Novo, and Net DNA Synthesis", in Methods Enzymol., 146A (New York: Academic Press, 1987), pp. 329–40]. One standard method to determine the proliferation (mitogenic) activity of a compound or composition is to assay it in vitro for its ability to induce anchorage-independent growth of nontransformed cells in soft agar [e.g., Rizzino, 1987, supra]. Other mitogenic activity assay systems are also known [e.g., Gimenez-Gallego et al., 1986, supra; Canalis et al., 1988, supra; Dickson et al., 1987, supra]. Mitogenic effects of agents are frequently very concentration-dependent, and their effects can be reversed at lower or higher concentrations than the optimal concentration range for mitogenic effectiveness.

Transforming Factor—as used herein, refers to any peptide, polypeptide, protein, or any other compound or composition which induces differentiation of a cartilage repair cell into a chondrocyte. The ability of the compound or composition to induce or stimulate production of cartilage-specific proteoglycans and type II collagen by cells can be determined by in vitro assays known in the art [Seyedin et al., Proc. Natl. Acad. Sci. USA, 82, pp. 2267–71 (1985); Seyedin et al., Path. Immunol. Res., 7, pp. 38–42 (1987)].

Transforming Growth Factor Beta (TGF-β)—any member of the family of TGF-β polypeptides [Derynck, R. et al., Nature, 316, pp. 701–705 (1985); Roberts et al., "The transforming growth factor-β's", In Peptide growth factors and their receptors I (Berlin: Springer Verlag, 1990), p. 419)] or derivatives thereof, obtained from natural, synthetic or recombinant sources, which exhibits the characteristic TGF-β ability to stimulate normal rat kidney (NRK) cells to grow and form colonies in a soft agar assay [Roberts et al., "Purification of Type β Transforming Growth Factors From Nonneoplastic Tissues", in Methods for Preparation of Media, Supplements. and Substrata for Serum-Free Animal Cell Culture (New York: Alan R. Liss, Inc., 1984)] and which is capable of inducing transformation of cartilage repair cells into chondrocytes as evidenced by the ability to induce or stimulate production of cartilage-specific proteoglycans and type II collagen by cells in vitro [Seyedin et al., 1985, supra].

This invention relates to compositions and methods for treating defects or lesions in cartilage and bone. The compositions of this invention comprise matrices having pores sufficiently large to allow cells to populate the matrices.

For use in the repair of cartilage as in superficial defects or the cartilage layer in a full-thickness defect, the matrix contains an anti-angiogenic agent which has biological activity that prevents blood vessel growth into the cartilage tissue, thereby preventing bone formation and inadequate repair of the cartilage tissue. The matrix may also contain a proliferation agent to stimulate the proliferation of cartilage repair cells in the matrix. Preferably, the proliferation agent also serves as a chemotactic agent to attract cartilage repair cells to the matrix. Alternatively, the matrix may contain a chemotactic agent in addition to the proliferation agent. In one preferred embodiment of this invention, the matrix also contains an appropriate concentration of a transforming factor, the transforming factor being contained within or in association with a delivery system which effects release of the transforming factor at the appropriate time to transform the proliferated cartilage repair cells in the matrix into chondrocytes which produce stable cartilage tissue. The matrix may also contain a cell adhesion promoting factor.

For cartilage repair matrices to be used in the repair of full-thickness defects a chemotactic or proliferation agent may not be required and it may not be necessary to substantially delay the release of the transforming factor. In full thickness defects, adequate access exists to the repair cells in the bone underneath and there is no need to recruit synovial cells for this purpose. The repair cells from the bony space will migrate quickly into the cartilage defect site. Proliferation agents and chemotactic factors may be included, however, if desired, especially where the defect area is large. Because repair cells will quickly populate the defect site, substantially delayed exposure to transforming factor is not as important as in superficial defects where more time is required to attract and proliferate repair cells. However, if the defect area is large, the transforming factor may be sequestered to ensure sufficient proliferation of repair cells throughout the defect area prior to exposure to the transforming factor. In addition, for the treatment of full-thickness defects the anti-angiogenic agent and the transforming factor may be contained in the matrix both in free form and associated with a delivery system to provide sustained concentrations over time.

In the case of full-thickness defects that extend significantly into the underlying bone, the bone portion of the defect in preferably filled with a bone repair matrix prior to filling the cartilage portion of the defect with a cartilage repair matrix of this invention.

Matrix materials useful in the methods and compositions of this invention for filling or otherwise dressing the cartilage or bone defects include fibrinogen (activated with thrombin to form fibrin in the defect or lesion), collagen, agarose, gelatin and any other biodegradable material which forms a matrix with pores sufficiently large to allow cartilage or bone repair cells to populate and proliferate within the matrix and which can be degraded and replaced with cartilage or bone during the repair process. In some instances, calcium phosphate containing compounds, such as tricalcium phosphate, and hydroxyapatite, as well as other calcium salts that form solid matrices, may be used alone or in combination with other biodegradable matrix materials in treating bone defects.

The matrices useful in the compositions and methods of this invention may be preformed or may be formed in situ, for example, by polymerizing compounds and compositions such as fibrinogen to form a fibrin matrix. Matrices that may be preformed include collagen (e.g., collagen sponges and collagen fleece), chemically modified collagen, gelatin beads or sponges, a gel-forming substance such as agarose, and any other gel-forming or composite substance that is composed of a matrix material that will fill the defect and allow cartilage or bone repair cells to populate the matrix, or mixtures of the above.

In one embodiment of this invention, the matrix is formed using a solution of fibrinogen, to which is added thrombin to initiate polymerization shortly before use. A fibrinogen concentration of 0.5–5 mg/ml of an aqueous buffer solution may be used. Preferably, a fibrinogen solution of 1 mg/ml of an aqueous buffer solution is used. Polymerization of this fibrinogen solution in the defect area yields a matrix with a pore size sufficiently large (e.g., approximately 50–200 $\mu$m) so that cartilage or bone repair cells are free to populate the matrix and proliferate in order to fill the volume of the defect that the matrix occupies. Preferably, a sufficient amount of thrombin is added to the fibrinogen solution shortly before application in order to allow enough time for the surgeon to deposit the material in the defect area prior to completion of polymerization. Typically, the thrombin concentration should be such that polymerization is achieved within a few to several (2–4) minutes since exposure of cartilage to air for lengthy periods of time has been shown to cause damage [Mitchell et al., *J. Bone Joint Surg.*, 71A, pp. 89–95 (1989)]. Excessive amounts of thrombin should not be used since thrombin has the ability to cleave growth factor molecules and inactivate them. Thrombin solutions of 10–500 units per ml, and preferably 100 units per ml, of an aqueous buffer solution may be prepared for addition to the fibrinogen solution. In a preferred embodiment of this invention, approximately 20 $\mu$l of thrombin (100 U/ml) are mixed with each ml of a fibrinogen solution (1 mg/ml) approximately 200 seconds before filling the defect. Polymerization will occur more slowly if a lower concentration of thrombin is added. It will be appreciated that the amount of thrombin solution needed to achieve fibrin polymerization within 2–4 minutes can be given only approximately, since it depends upon the environmental temperature, the temperature of the thrombin solution, the temperature of the fibrinogen solution, etc. Alternatively, where convenient, the thrombin may be added by placing it on top of the matrix solution after the solution has been placed in the defect site and allowing it to diffuse through the solution. The polymerization of the thrombin-activated matrix solution filling the defect is easily monitored by observing the thrombin-induced polymerization of an external sample of the fibrinogen solution. Preferably, in the compositions and methods of this invention, fibrin matrices are formed from autologous fibrinogen molecules, i.e., fibrinogen molecules derived from the blood of the same mammalian species as the species to be treated. Non-immunogenic fibrinogen from other species may also be used.

Matrices comprising fibrin and collagen or, more preferably, fibrin and gelatin may also be used in the compositions and methods of this invention. Collagenous matrices may also be used in repairing cartilage defects, including full thickness defects. In a preferred embodiment of this invention, more solid matrices, such as those containing hydroxyapatite or tricalcium phosphate, are used in repairing the bone portion of deep full-thickness defects.

When collagen is used as a matrix material, sufficiently viscous solutions can be made, e.g., using Collagen-Vliess® ("fleece"), Spongostan®, or gelatine-blood-mixtures, and there is no need for a polymerizing agent. Collagen matrices may also be used with a fibrinogen solution activated with a polymerizing agent so that a combined matrix results.

Polymerizing agents may also be unnecessary when other biodegradable compounds are used to form the matrix. For example, Sepharose® solutions may be chosen that will be liquid matrix solutions at 39°–42° C. and become solid (i.e., gel-like) at 35°–38° C. The Sepharose should also be at concentrations such that the gel filling the defect has a mesh size to allow bone or cartilage repair cells to freely populate the matrix and defect area.

In the compositions of this invention used in cartilage repair, one or more anti-angiogenic agents is added to the matrix solution in an appropriate concentration range to prevent blood vessel growth into the cartilage tissue. Anti-angiogenic agents that may be used include any agent with biological activity that prevents ingrowth of blood vessels from the underlying bone tissue into the cartilage tissue. Some examples of anti-angiogenic agents that may be useful for this invention are set forth above. The anti-angiogenic agent should be freely available to provide immediate activity in the matrix and may also be present in a sustained-release form, e.g., associated with a delivery system as described below, for prolonged activity.

One or more proliferation (mitogenic) agents may also be added to the matrix solution used in cartilage repair. The proliferation agent or agents should be present in an appropriate concentration range to have a proliferative effect on cartilage repair cells in the matrix filling the defect. Preferably, the same agent should also have a chemotactic effect on the cells (as in the case of TGF-β); however, a factor having exclusively a proliferative effect may be used. Alternatively, to produce chemotactic cell immigration, followed by induction of cell proliferation, two different agents may be used, each one having just one of those specific effects (either chemotactic or proliferative).

Proliferation (mitogenic) agents useful in the compositions and methods of this invention for stimulating the proliferation of cartilage repair cells include transforming growth factors ("TGFs") such as TGF-αs and TGF-βs; insulin-like growth factor ("IGF I"); acidic or basic fibroblast growth factors ("FGFs"); platelet-derived growth factor ("PDGF"); epidermal growth factor ("EGF"); hemopoietic growth factors, such as interleukin 3 ("IL-3") and bone morphogenic proteins ("BMPs"), such as bone morphogenic protein-2 ("BMP-2") [Rizzino, 1987, supra; Canalis et al., supra, 1988; *Growth factors in biology and medicine, Ciba Foundation Symposium,* 116 (New York: John Wiley & Sons, 1985); Baserga, R., ed., *Cell growth and division* (Oxford: IRL Press, 1985); Sporn, M. A. and Roberts, A. B., eds., *Peptide growth factors and their receptors,* Vols. I and II (Berlin: Springer-Verlag, 1990)]. However, these particular examples are not limiting. Any compound or composition which is capable of stimulating the proliferation of cells as demonstrated by an in vitro assay for cell proliferation is useful as a proliferation agent in this invention. Such assays are known in the art [e.g., Canalis et al., 1988, supra; Gimenez-Gallego et al., 1986, supra; Dickson et al., 1987, supra; Rizzino, 1987, supra].

Chemotactic agents useful in the compositions and methods of this invention for attracting cartilage repair cells to the cartilage defect include, for example, TGF-βs, FGFs (acid or basic), PDGF, tumor necrosis factors (e.g., TNF-α, TNF-β) and proteoglycan degradation products, such as glycosaminoglycan chains [Roberts et al. (1990), supra; *Growth factors in biology and medicine, Ciba Foundation Symposium,* 116 (New York, John Wiley & Sons, 1985); R. Baserga, ed., *Cell growth and division* (Oxford: IRL Press, 1985)]. Assays to determine the chemotactic ability of polypeptides and other compounds are known in the art [e.g., Postlewaite et al., 1987, supra; Wahl et al., 1987, supra; Moore et al., 1989, supra].

In a preferred embodiment of this invention, the matrix used in cartilage repair contains TGF-β as the proliferation agent and as the chemotactic agent. In particular, TGF-βI or TGF-βII may be used as the proliferation and chemotactic agent. Other TGF-β forms (e.g., TGF-βIII, TGF-βIV, TGF-βV, etc.) or polypeptides having TGF-β activity [see Roberts, 1990, supra] may also be useful for this purpose, as well as other forms of this substance to be detected in the future, and other growth factors. For use as the proliferation agent and chemotactic agent, TGF-β molecules are dissolved or suspended in the matrix at a concentration of preferably 2–50 ng/ml of matrix solution, and most preferably, 2–10 ng/ml of matrix solution. Alternatively, BMP-2 may be used at a concentration of less than 1 ng/ml as a proliferation agent. It will be appreciated that the preferred concentration of TGF-β or BMP-2 that will stimulate proliferation of cartilage repair cells may vary with the particular animal to be treated.

A transforming factor or factors may also be present in the matrix solution used in cartilage repair so that after cartilage repair cells have populated the matrix, the transforming factor will be released into the defect site in a concentration sufficient to promote differentiation (i.e., transformation) of the cartilage repair cells into chondrocytes which form new stable cartilage tissue. Proper timing of the release of the transforming factor is particularly important if the transforming factor can inhibit or interfere with the effectiveness of the proliferation agent [see Roberts et al. (1990), supra].

Transforming factors useful in the compositions and methods of this invention to promote cartilage repair include any peptide, polypeptide, protein or any other compound or composition which induces differentiation of cartilage repair cells into chondrocytes which produce cartilage-specific proteoglycans and type II collagen. The ability of a compound or composition to induce or stimulate production of cartilage-specific proteoglycans and type II collagen in cells can be determined using assays known in the art [e.g., Seyedin et al., 1985, supra; Seyedin et al., 1987, supra]. The transforming factors useful in the compositions and methods of this invention include, for example, TGF-βs, TGF-αs, FGFs (acid or basic) and BMPs, including BMP-2. These transforming factors may be used singly or in combination. Dimers and multimers of these factors may also be used. In addition, TGF-β may be used in combination with EGF.

Where necessary, the properly timed release of the transforming factor may be achieved by packaging the transforming factor in or with an appropriate delivery system. Delivery systems useful in the compositions and methods of this invention include liposomes, bioerodible polymers, carbohydrate-based corpuscles, water-oil emulsions, fibers such as collagen which may be chemically linked to heparin sulfate proteoglycans or other such molecules to which transforming factors bind spontaneously, and osmotic pumps. Delivery systems such as liposomes, bioerodible polymers, fibers with bound transforming factors and carbohydrate-based corpuscles containing the transforming agent may be mixed with the matrix solution used to fill the defect. These systems are known and available in the art [see P. Johnson and J. G. Lloyd-Jones, eds., *Drug Delivery Systems* (Chichester, England: Ellis Horwood Ltd., 1987)]. Liposomes may be prepared according to the procedure of Kim et al., *Biochem. Biophys. Acta,* 728, pp. 339–348 (1983). Other liposome preparation procedures may also be used. Additional factors for stimulating chondrocytes to synthesize the cartilage tissue components may be included with the transforming factor in the delivery system. The timing of transforming factor availability should be coordinated with the speed in which repair cells will proliferate and fill the defect site to be treated. Where substantial delay of the release of the transforming factor is not required, the transforming may be included in the matrix in both a freely available form and associated with a delivery system to provide sustained release at the appropriate concentration.

In a preferred embodiment of this invention, the matrix used in cartilage repair contains an anti-angiogenic agent, TGF-β or BMP as the proliferation and chemotactic agent, and TGF-β or BMP packaged in a delivery system as the transforming factor. In particular, TGF-βI or TGF-βII or BMP-2 may be used as the proliferation and chemotactic agent and as the transforming factor. Other TGF-β forms (e.g., TGF-βIII, TGF-βIV, TGF-βV, or any member of the TGF-β superfamily) or polypeptides having TGF-β activity (see Roberts, 1990, supra) may also be useful for this purpose, as well as other forms of this substance to be detected in the future, and other growth factors. The antiangiogenic agent is preferably contained within the delivery system containing the transforming concentration of TGF-β or BMP as well as in free form in the matrix.

In a preferred embodiment for cartilage repair, a TGF-β concentration of preferably 2–50 ng/ml of matrix solution, and most preferably, 2–10 ng/ml of matrix solution, is used as a proliferation agent and as a chemotactic agent. A substantially higher concentration of TGF-β is also present in a subsequently releasable form in the matrix composition as a transforming factor. Preferably, the subsequent concentration of TGF-β is greater than 200 ng/ml of matrix and, most preferably, is greater than or equal to 500 ng/ml of matrix. Alternatively, BMP may be used as a transforming factor at a preferable concentration of 100–2000 ng per ml. It will be appreciated that the preferred concentration of TGF-β or BMP to induce differentiation of cartilage repair cells may vary with the particular animal to be treated.

It is necessary to stagger the exposure of the cartilage repair cells to the two concentration ranges of TGF-β, since TGF-β at relatively high concentrations (e.g., greater than 200 ng/ml of matrix solution) may not only transform cartilage repair cells into chondrocytes, but also will inhibit chemotactic attraction of cartilage repair cells; whereas at relatively low concentrations (e.g., 2–10 ng/ml), TGF-β attracts cartilage repair cells and stimulates their proliferation, but will not induce transformation of cartilage repair cells into chondrocytes which produce cartilage tissue.

In a preferred embodiment of this invention, where necessary to obtain the sequence of chemotaxis and proliferation, followed by transformation, TGF-β is present both in a free, unencapsulated form and in an encapsulated, or otherwise sequestered, form in the matrix. Preferably, for the purpose of attracting and inducing proliferation of cartilage repair cells in the matrix and defect area, TGF-β molecules are dissolved or suspended in the matrix at a concentration of 2–10 ng/ml of matrix solution. To promote transformation of cartilage repair cells in the matrix into chondrocytes, TGF-β molecules are also present in the matrix sequestered in multi vesicular liposomes according to the method of Kim et al., 1983, supra, at a concentration of greater than 200 ng/ml of matrix solution, and preferably at a concentration of 500–800 ng/ml. The TGF-β-loaded liposomes are disrupted when the attracted cartilage repair cells have populated the matrix and have started to degrade the matrix. During the degradation of the matrix, the cartilage repair cells ingest and/or degrade the liposomes, resulting in the release of TGF-β at concentrations sufficient to induce the transformation of cartilage repair cells into chondrocytes.

The required two-stage delivery of chemotactic and proliferating versus transforming concentrations of TGF-β may also be achieved by combining transforming concentrations of TGF-β with a bioerodible polymer. Alternatively, a pump, and preferably an implanted osmotic pump, may be used to control the concentration of TGF-β in the defect and matrix. In this embodiment of the invention, the pump controls the concentration of TGF-β in the matrix, i.e., the pump may release TGF-β at an initial chemotactic and proliferation stimulating concentration and at a subsequent transforming concentration. Preferably, the transforming concentration of TGF-β is delivered by the pump approximately 1 to 2 weeks post-operatively. Delivery of the transforming factor into the defect volume is preferably localized to the matrix in the defect site.

The proliferation agents and, when used, the transforming factors in the compositions of this invention are applied in the defect site within the matrix. Their presence is thus restricted to a very localized site. This is done to avoid their free injection or infusion into ajoint space. Such free infusion may produce the adverse effect of stimulating the cells of the synovial membrane to produce joint effusion.

In certain embodiments of this invention for treating full-thickness defects, delayed exposure to transforming factor is not necessary. In many full-thickness defects, adequate access to repair cells exists and delayed exposure to transforming factor is less critical than with superficial defects where more time is required to attract and proliferate repair cells. However, in deep defects, it may be desirable to delay the exposure to transforming factor to allow repair cells to populate the entire defect site.

In the compositions of this invention used for bone repair, one or more angiogenic factors is may be added to the matrix solution to stimulate the formation and ingrowth of blood vessels and associated cells (e.g., endothelial, perivascular, mesenchymal and smooth muscle cells) and of basement membranes in the area of the bone defect. Angiogenic factors useful in the compositions and methods of this invention for stimulating vascularization throughout the deposited matrix in the area of the bone defect include bFGF, TGF-β, PDGF, TNF-α, angiogenin or angiotropin. Heparin sulfate has been found to enhance the angiogenic activity of bFGF. In a preferred embodiment of this invention, bFGF is dissolved, suspended or bound in a matrix at a concentration of 5–10 ng/ml of matrix solution along with an amount of heparin sulfate sufficient to enhance the angiogenic activity of bFGF. The preferred concentrations for other angiogenic factors are: 5 ng/ml of matrix solution for TGF-β, 10 ng/ml of matrix solution for TNF-α, and 10 ng/ml of matrix solution for PDGF. However, bFGF in combination with heparin sulfate is the most preferred angiogenic factor among the above named angiogenic factors.

An osteogenic factor may also be present in the matrix solution used for bone repair so that after blood vessels and associated cells have populated the matrix, the osteogenic factor is released into the bone defect site as the matrix is degraded in a concentration sufficient to promote a process leading to the eventual development of osteoblasts and osteocytes. The osteogenic factor is sequestered or packaged in an appropriate delivery system within the matrix and is released as the matrix is degraded. The delivery systems used in the cartilage repair compositions are useful in the bone repair compositions of this invention, e.g., liposomes or carbohydrate-based corpuscles (see supra). In one embodiment of this invention, the matrix used in bone repair contains TGF-β packaged in a delivery system as the osteogenic factor, at a preferable concentration of 100 ng/rnl of matrix solution. Lower and higher concentrations of TGF-β may be used. In another embodiment, the matrix used for bone repair contains BMP-2 packaged in a delivery system as the osteogenic factor, at a preferable concentration of 100–2000 ng/ml of matrix solution. In still another embodiment, the matrix contains FGF at an appropriate concentration packaged in a delivery system as an osteogenic factor.

Osteogenic factors useful in the bone repair compositions of this invention include any peptide, polypeptide, protein or any other compound or composition which induces differentiation of bone repair cells into bone cells, such as osteoblasts and osteocytes, which produce bone tissue. The osteogenic factors useful in this invention include proteins such as TGF-β [Sampath, T. R. et al., *J Biol. Chem.*, 265(22), pp. 13198–13205 (1990)], osteogenin [Luyten, F. P. et al., *J. Biol. Chem.*, 264(15), pp. 13377–80 (1989)], bone morphogenic protein (BMP) [Wang, E. et al., *Proc. Natl. Acad. Sci. USA*, 87, pp. 2220–24 (1990)], FGF, and TGF-β combined with epidermal growth factor (EGF).

The differentiation of mesenchymal cells induced by an osteogenic factor may include the formation of intermediary tissues such as fibrous, hyaline and calcified cartilage; and endochondral ossification, which leads to the formation of woven bone tissue, which will become remodeled and transformed into mature lamellar bone tissue. In some instances, bone may be formed directly from mesenchymal cells without the appearance of an intermediary tissue. Within the matrix, the process of bone tissue formation usually occurs 3 to 4 weeks after blood vessels have formed and infiltrated the matrix in response to the angiogenic factor present in the matrix. Although bone will grow into the bone defect site in the absence of added angiogenic and osteogenic factors (use of at least a matrix material is desirable in large defects), the use of such factors substantially speeds up the repair process.

The matrix compositions described in this invention for repairing the bone portion of a full-thickness defect in joints are also useful in treating any defect in bone tissue as is desirable. Such defects include bone fractures, joint fractures, non-unions and delayed unions, percutaneous arthrodesis, pseudo-arthrosis and bone defects resulting from congenital defects, trauma, tumor infection, degenerative disease and other causes of loss of skeletal tissue. The bone repairing matrix compositions are also useful for prosthesis implantation and enhancement of prosthesis stability, enhancement of osseointegration of implant materials used for internal fixation procedures, stabilization of dental implant materials, healing acceleration of ligament insertion, and spine or other joint fusion procedures.

Fibronectin or any other compound, including peptides as small as tetrapeptides, that contain the amino acid sequence Arg-Gly-Asp, may be used as cell adhesion promoting factors [Ruoslathi et al., *Cell*, 44, pp. 517–18 (1986)] in order to enhance the initial adhesion of cartilage or bone repair cells to a matrix deposited in a defect site. Fibrin and certain collagen matrices already contain this sequence [Ruoslathi et al., 1986, supra]. When other biodegradable matrices are used, such cell adhesion promoting factors may be mixed with the matrix material before the matrix is used to fill or dress the defect. Peptides containing Arg-Gly-Asp may also be chemically coupled to the matrix material (e.g., to its fibers or meshes) or to a compound added to the matrix, such as albumin.

The compositions hereinbefore described are useful in methods to induce cartilage or bone formation at a selected site of defect in cartilage or bone tissue of an animal.

The methods of this invention allow for a treatment of cartilage and bone defects in animals, including humans, that is simple to administer and is restricted in location to an affected joint area. The entire treatment may be carried out by arthroscopic, open surgical or percutaneous procedures.

To carry out the methods of treating defects or lesions in cartilage and bone according to this invention, a defect or lesion is identified, prepared, and filled with the matrix compositions according to this invention.

For cartilage repair, the matrix composition may contain an anti-angiogenic agent to prevent ingrowth of blood vessels. A proliferation (mitogenic) agent may also be present in the matrix composition at an appropriate concentration to stimulate the proliferation of cartilage repair cells in the matrix and defect or lesion. The same agent may also, at this concentration, serve as a chemotactic agent to attract cartilage repair cells, provided that the factor used has a combined effect with respect to cell proliferation and chemotaxis (as does TGF-β at 2–10 ng/ml of matrix). Alternatively, two different agents may be present in the matrix, one with a specific proliferative effect, and the other with a specific chemotactic effect. In an alternative embodiment, after the defect area is dressed with the matrix, the anti-angiogenic agent and, if desired, a proliferation agent and a chemotactic agent, may be injected directly into the matrix-filled defect area. Injection should be localized to the matrix and filled defect area to avoid exposure of cells of the synovial membrane to growth factors which could lead to cell proliferation and joint effusion.

After the defect site is dressed with the matrix composition (and, in the case of fibrin matrices, once the matrix has solidified) and, if required, the anti-angiogenic agent or the proliferation agent has been injected into the matrix-filled defect site, the joint capsule and skin incisions may be closed and the arthroscopy or open surgery terminated.

In a subsequent step of cartilage repair, the cartilage repair cells in the matrix are exposed to a transforming factor at the appropriate time at a concentration sufficient to transform the cartilage repair cells into chondrocytes which produce stable cartilage tissue. This may be accomplished by including an appropriate delivery system containing the transforming factor within the matrix composition as described above. Alternatively, the transforming agent may be delivered by injection directly or by an osmotic pump into the matrix-filled defect area at the appropriate time. In a superficial cartilage defect with no access to repair cells from bone tissue, the transforming concentration should be made available to the cells approximately 1 to 2 weeks following the initial implantation of the matrix into the defect area. In a full-thickness cartilage defect, depending on the size of the defect, the transforming factor may be made available earlier. Additional factors may be added to the delivery system or directly injected in order to better promote synthesis of the cartilage matrix components at this time point. Also, additional anti-angiogenic agent may be included in the delivery system or directly injected.

Cartilage or bone defects in animals are readily identifiable visually during arthroscopic examination of the joint or during simple examination of the lesion or defect during open surgery. Cartilage or bone defects may also be identified inferentially by using computer aided tomography (CAT scanning) X-ray examination, magnetic resonance imaging (MRI) analysis of synovial fluid or serum markers, or by any other procedure known in the art.

Once a defect has been identified, the surgeon may elect to surgically modify the defect to enhance the ability of the defect to physically retain the solutions and matrix material that are added in the treatment methods described herein. Preferably, instead of having a flat or shallow concave geometry, the defect has or is shaped to have vertical edges or is undercut in order to better retain the solutions and matrix materials added in the treatment methods described herein.

According to the methods of this invention, the bone defect site of a full-thickness defect may be filled up to the calcified cartilage layer at the bone-cartilage interface with a bone repair matrix composition such that a flat plane is formed. Filling the bone defect with a bone repair matrix is particularly useful for defects several millimeters or more deep. The bone repair matrix composition may contain an angiogenic factor and an osteogenic factor packaged in an appropriate delivery system.

The remaining cartilage portion of the defect is completely filled with a matrix composition used to stimulate cartilage repair. The composition for cartilage repair comprises a matrix material containing an anti-angiogenic agent and, if desired, a proliferation agent and a chemotactic agent. Anti-angiogenic agents useful in the compositions and methods of this invention include any agents with biological activity capable of inhibiting vascularization. This invention contemplates that the anti-angiogenic agent may comprise one or more molecules capable of inhibiting angiogenesis. The composition used in this step may also contain a transforming factor packaged in a delivery system and, if appropriate, in free form as well. In the most preferred method of cartilage repair of the invention, the matrix contains an anti-angiogenic factor (in free form and packaged in or associated with a delivery system for sustained release), a proliferation agent, a chemotactic agent (which may be identical to the proliferation agent), and a transforming factor that is packaged in or associated with a delivery system that releases the transforming factor at a time that the repair cells populating the matrix have begun remodeling the intercellular substance. Preferred compositions are described above.

As described in U.S. Pat. No. 5,270,300, the bone-cartilage interface of a full-thickness defect may be separated with a physical membrane, preferably a biodegradable membrane, which is impermeable to cells (e.g., pore sizes less than 5 $\mu$m), prior to filling the cartilage portion of a full thickness defect. The membrane is placed over the matrix-filled bone defect, and the edges of the membrane must be sealed to the perimeter of the defect in the region of the cartilage-bone junction to prevent vascular ingrowth into the cartilage defect area. In this method, repair cells from the bone area are not readily available to populate the cartilage defect area and a proliferation agent and/or chemotactic agent is therefore necessary in the cartilage repair matrix to attract and stimulate proliferation of repair cells from the synovium.

In a preferred embodiment of this invention for treating full-thickness defects, no membrane is placed at the bone-cartilage interface. The bone portion of the defect may or may not be filled with a bone repair composition, as desired. The cartilage portion of the defect is filled with a matrix composition containing an anti-angiogenic agent and a transforming factor and, if desired, a proliferation agent, and/or a chemotactic agent, as discussed above. The anti-angiogenic agent in the cartilage repair matrix composition acts as a functional barrier to prevent the ingrowth of blood vessels and the formation of bone in the cartilage area, avoiding the necessity of a physical membrane and allowing the migration of repair cells from the bone area.

In another embodiment of the methods of this invention for treating full-thickness defects, the bone-cartilage interface is separated by a transient biological membrane, created at the bone-cartilage interface by a heated instrument. A heated instrument may be applied to locations of bleeding to coagulate the blood and form a layer of precipitated protein, thus resulting in a biological physical barrier that prevents ingrowth of blood vessels and bone tissue formation in the defect site. Examples of heated instruments include, but are not limited to heated scalpel blade, heated scissors or heated forceps. The instrument should be heated to a temperature of about 200° C. The heated instrument should be applied to the base of the full thickness defect. In another embodiment, heat may be applied by a $CO_2$, $N_2$ or Neodynium-Yag laser. This heat-created transient biological membrane at the bone-cartilage interface may be employed in addition to or in lieu of including an anti-angiogenic agent in the cartilage repair matrix. When the heat treatment method is used, a proliferation agent and/or chemotactic agent should be included in the cartilage repair matrix.

Chemical measures may enhance matrix adhesion. Such measures include degrading the superficial layers of cartilage proteoglycans on the defect surface to expose the collagen fibrils of the cartilage so that they may interact with the collagen fibrils of the matrix (when a collagenous matrix is used) or with the fibrin fibrils of the matrix (when a fibrin matrix issued). The proteoglycans on the surface of the cartilage not only tend to interfere with adherence of a fibrin or other biodegradable matrix to the cartilage, but also inhibit thrombin activity locally. Advantageously, proteoglycan degradation products may also have a chemotactic effect on repair cells [Moore, A. R. et al., *Int. J. Tiss. Reac.*, XI(6), pp. 301–307 (1989)].

According to one embodiment of the methods of this invention, the surface of the defect is dried by blotting the area using sterile absorbent tissue, and the defect volume is filled with a sterile enzyme solution for a period of 2–10 minutes to degrade the proteoglycans present on the surface of the cartilage and locally within approximately 1 to 2 $\mu$m deep from the surface of the defect. Various enzymes may be used, singly or in combination, in sterile buffered aqueous solutions to degrade the proteoglycans. The pH of the solution should be adjusted to optimize enzyme activity.

Enzymes useful to degrade the proteoglycans in the methods of this invention include chondroitinase ABC, chondroitinase AC, hyaluronidase, pepsin, trypsin, chmotrypsin, papain, pronase, stromelysin and Staph V8 protease. The appropriate concentration of a particular enzyme or combination of enzymes will depend on the activity of the enzyme solution.

In a preferred embodiment of this invention, the defect is filled with a sterile solution of chondroitinase AC at a concentration of 1 U/ml and digestion is allowed to proceed for 4 minutes. The preferred concentration of chondroitinase AC is determined according to the procedure described in Example 1. Any other enzyme used should be employed at a concentration and for a time period such that only superficial proteoglycans down to a depth of about 1–2 $\mu$m are degraded.

The amount of time the enzyme solution is applied should be kept to a minimum to effect the degradation of the proteoglycans predominantly in the repair area. For chondroitinase ABC or AC at a concentration of 1 U/ml, a digestion period longer than 10 minutes may result in the unnecessary and potentially harmful degradation of the proteoglycans outside the defect area. Furthermore, digestion times longer than 10 minutes contribute excessively to the overall time of the procedure. The overall time for the procedure should be kept to a minimum especially during open arthrotomy, because cartilage may be damaged by exposure to air [Mitchell et al., (1989), supra]. For these reasons, in the embodiments of the methods of this invention that include the step of degradation of proteoglycans by enzymatic digestion, digestion times of less than 10 minutes are preferred and digestion times of less than 5 minutes are most preferred.

According to the methods of this invention, after the enzyme has degraded the proteoglycans from the surface of the defect, the enzyme solution should be removed from the defect area. Removal of the enzyme solution may be effected by using an aspirator equipped with a fine suction tip followed by sponging with cotonoid. Alternatively, the enzyme solution may be removed by sponging up with cotonoid alone.

Following removal of the enzyme solution, the defect should be rinsed thoroughly, preferably three times, with sterile physiologic saline (e.g., 0.15M NaCl). The rinsed defect site should then be dried. Sterile gauze or cottonoid may be used to dry the defect site.

The adhesion of the matrix to the cartilage of the defect can also be enhanced by using fibrin glue (i.e., blood factor XIII or fibrin stabilization factor) to promote chemical bonding (cross-linking) of the fibrils of the matrix to the cartilage collagen fibrils on the defect surface [see Gibble et al., *Transfusion*, 30(8), pp. 741–47 (1990)]. The enzyme transglutaminase may be used to the same effect [see e.g., Ichinose et al., *J. Biol. Chem.*, 265(23), pp. 13411–14 (1990); "Transglutaminase," Eds: V. A. Najjar and L. Lorand, Martinus Nijhoff Publishers (Boston, 1984)]. Other compounds that can promote adhesion of extracellular materials may also be used.

Treatment of periodontal disease may be also aided with the methods and compositions of this invention. For example, in the treatment of disease such as paradontitis, in which the periodontal ligament recesses and toothnecks are exposed, the regeneration of periodontal connective tissue can be aided. In particular, the periodontal connective tissue, i.e., ligament, space is filled with a biodegradable matrix containing one or more factors to stimulate periodontal tissue formation, such as IGF-1 or FGF, and one or more anti-epithelial factors to inhibit epithelium formation, such as an inhibitor for epidermal growth factor (EGF), anti-basement membrane antibodies, vitamin A inhibitors, anti-retinol, and matrices enriched with fibronectin. The anti-epithelial factor should be in free form and packaged in or associated with a delivery system to provide sustained release in the area filled by the matrix. Preferable matrix materials are crosslinked gelatin or collagen matrices with sufficient ability to adhere to the tooth and gum.

Bone regeneration, e.g., following loss of teeth can also be aided by the methods and compositions of this invention. When a tooth is lost, the bony compartment in which the tooth was anchored is usually atrophic and recessed. This area, i.e., the maxillar or mandibular ridge, must be built up and reformed prior to positioning of a dental implant. However, bony regrowth is usually prevented by the rapidly growing connective tissue around it. This can be prevented by using a bone repair matrix such as those described above, and including in the matrix an effective amount of one or more inhibitors of migration and/or proliferation and/or differentiation of connective tissue cells. For example, a matrix containing an angiogenic factor, an osteogenic factor associated with a delivery system, and an anti-connective tissue factor, such as factors inhibiting mesenchymal cell proliferation, may be placed in the area to be built up with bone tissue. To promote the re-formation of connective tissue in the surrounding periodontal connective tissue compartment a biodegradable matrix containing factors to stimulate the migration, proliferation and differentiation of connective tissue stem and precursor cells, such as IGF-1 and FGF, may be placed in the spaces within the peridontium. The connective tissue matrix may also contain an anti-epithelial factor.

Another aspect of this invention is the prevention of periarticular calcification and ossification of the connective tissue compartments around bone which occurs, for example, after joint replacements such as total hip replacements. A matrix containing anti-bone factors such as anti-angiogenic agents, antibodies to TGF-β and BMP compounds, or combinations thereof, in free form and associated with or packaged in a delivery system to provide sustained release, may be applied in the periarticular connective tissue space to prevent calcification and the formation of bony tissue.

A further application of this invention is the prevention of bone tissue ingrowth into a fracture site which extends through the cartilaginous growth plate in young animals and children, which may occur when distal ends of long bones are fractured. As with the prevention of ossification of connective tissue compartments around bone, a matrix containing anti-bone factors such as an anti-angiogenic factor, antibodies to TGF-β and BMP compounds, or combinations thereof can be used to fill the fracture gap in the area of the cartilaginous growth plate.

In order that the invention described herein may be more fully understood, the following examples are set forth. It should be understood that these examples are for illustrative purposes and are not to be construed as limiting this invention in any manner.

EXAMPLE 1

Enzyme Testing for Proteoglycan Removal

In order to promote and improve matrix adherence along superficial defect surfaces of articular cartilage tissue, proteoglycan molecules within the superficial cartilage matrix may be removed enzymatically, in order to expose the collagen fibrillar network to externally applied matrices and to migrating repair cells. Various proteases and glycosaminoglycan-degrading enzymes are suitable to be used for this purpose, but pH conditions should be controlled to provide maximal activity for each enzyme.

In this example, we tested chondroitinase ABC (0.5–5 U/ml) and trypsin (0.5–4%) for their ability to effect proteoglycan removal. Knee joints from freshly slaughtered rabbits, obtained from a local butcher, were employed. Mechanically-created superficial cartilage defects were exposed to the enzyme solutions for a period of 4 minutes. Solutions were then removed with absorbent tissue and the defect sites rinsed thoroughly with physiologic saline. Following this procedure, cartilage tissue was fixed immediately in 2% (v/v) glutaraldehyde solution (buffered with 0.05M sodium cacodylate, pH 7.4) containing 0.7% (w/v) ruthenium hexamine trichloride (RHT) for histological examination. The post-fixation medium consisted of a 1% RHT-osmium tetroxide solution (buffered with 0.1M sodium cacodylate). Tissue was dehydrated in a graded series of ethanol and embedded in Epon 812. Thin sections were cut, stained with uranyl acetate and lead citrate, and examined in an electron microscope. In these sections, RHT-fixed (i.e., precipitated) proteoglycans appeared as darkly-staining granules. Enzyme concentrations removing a superficial layer of proteoglycans no more than 1–2 μm in thickness were defined as optimal (deeper penetration of enzymes could affect the underlying chondrocytes). Chondroitinase ABC was found to be optimally active at a concentration of approximately 1 U/ml. Trypsin was found to be optimally active at a concentration of approximately 2.5%. The optimal activity range for other glycosaminoglycanases or proteases may be determined in a similar manner. Any buffer may be used in conjunction with the enzyme provided that it is nontoxic and that its maximal buffering capacity occurs at a pH value close to that required for maximal enzyme activity.

EXAMPLE 2

Matrix Adherence to Superficial Defects

The possibility of promoting matrix adhesion along defect surfaces by controlled enzyme digestion of superficial cartilage proteoglycans was investigated. Defects were created in the knee joints of three mature rabbits by cutting with a planing knife. These defects were not enzyme treated. The defects were filled with a fibrin matrix, formed by mixing 20 µl of a thrombin solution (100 U/ml aqueous buffer) with each ml of fibrinogen solution (1 mg/ml aqueous buffer) approximately 200 seconds before filling the defect. The rabbits were sacrificed after 1 month and the knee joints examined to determine the extent to which the fibrin matrix had adhered to the defect site. The results were compared to those achieved in rabbits whose defects had been treated with chondroitinase ABC (1 U/ml for 4 minutes) before the defect was filled with fibrin matrix (see Examples 3, 4 and 5).

The fibrin matrices deposited in defect areas left untreated with an enzyme exhibited low affinity to adhere to the defect surface. Following enzyme treatment, the sticking capacity of the fibrin matrices (determined indirectly by measuring mechanical strength to adhere, i.e., by testing the easiness with which the matrix could be pushed away manually with the tip of a forceps, and indirectly by noting the number of defects in which the matrix successfully remained sticking throughout the experiment) was significantly increased. The low affinity of matrices for the defect surfaces in the absence of enzyme treatment probably is due to a local inhibition of matrix adhesion by proteoglycan molecules and an inhibition of fibrin polymerization. Both of these effects are prevented by enzymatic removal of superficial proteoglycans along the defect surface area.

EXAMPLE 3

Application of Growth Factors to Defect Sites to Provide Chemotactic Stimulation of Repair Cell Migration into Defect Areas and Induction of Repair Cell Proliferation Various growth factors were tested for their usefulness in stimulating chemotactic migration of repair cells to the defect area in order to accomplish healing of the defect.

The growth factors employed included a) epidermal growth factor (EGF), b) basic fibroblast growth factor (bFGF), c) insulin-like growth factor I (IGF I), d) human growth hormone (hGH) and e) transforming growth factor-β (TGF-β) at concentrations of between 5–10 ng/ml.

Each of these factors was applied locally to defects produced in the knee following chondroitinase ABC treatment and rinsing as described in Example 2. A total of ten animals (two per growth factor) were utilized. Each growth factor was able to chemotactically attract or locally stimulate proliferation of repair cells to the defect surfaces sufficiently to completely cover the defect surfaces. However, the cells were only present on the surfaces of the defects, and in no instance was proliferation of the repair cells adequate to fill the defect volume.

(It is believed that the proteoglycan degradation products by themselves, i.e., without the addition of any other agent, exert a sufficient chemotactic effect to attract repair cells to the defect. Moore, A. R. et al, (Int. J. Tiss. Reac., XI(b), pp. 301–107, 1989] have shown that proteoglycan degradation products have chemotactic effects per se.)

EXAMPLE 4

Application to Defect Sites of Growth Factors Entrapped in Biodegradable Matrices to Provide Chemotactic stimulation of Repair Cell Migration into Defect Areas and Induction of Repair Cell Proliferation Since local application of a growth factor under the conditions of Example 3 in no instance induces repair cell proliferation adequate to fill the defect volume, the experiment was repeated using the same growth factors, but this time the growth factors were entrapped in biodegradable matrices. The biodegradable matrices used were fibrin, collagen and Sepharose. Sufficient quantities of matrices containing growth factor were applied to fill the defect volumes completely.

Fibrin matrices were formed by mixing 20 µl of a thrombin solution (100 U/ml of an aqueous buffer solution: Veronal acetate buffer, pH 7.0) with each ml of fibrinogen solution (1 mg/ml of an aqueous buffer solution: 0.05M Tris, pH 7.4, 0.1M NaCl) approximately 200 seconds prior to filling the defect. For collagen matrices, sufficiently viscous solutions were made using Colagen-Vliess® or gelatine-blood-mixtures. For Sepharose matrices, defects were filled with liquid solutions of Sepharose at 39–42° C. Upon cooling (3538° C.), a Sepharose matrix was formed in the defect.

Thirty rabbits (two for each type of matrix and growth factor) were utilized for this experiment. In all cases where the deposited matrix remained adherent to the defect, it became completely populated by fibroblast-like repair cells. This situation was found to exist as early as eight to ten days postoperatively. No further changes occurred in the structural organization of the repair tissue up to four weeks post-operatively, except that the biodegradable matrices became remodeled by the repair cells and replaced by a loose, connective tissue type of extracellular matrix.

Transformation of this tissue to cartilage tissue did not occur.

EXAMPLE 5

Application to Defect Sites of Growth Factors Entrapped in Biodegradable Matrices to Provide Chemotactic Stimulation of Repair Cell Migration into Defect Areas and Induction of Repair Cell Proliferation Followed by Timed, Local Release of a Transforming Factor at a Secondary Stage to Provide Transformation of the Defect Site into Hyaline Cartilage The observation that matrices within the defect volume were completely filled with repair cells following application of growth factor, and that these cells were able to remodel the deposited matrix (see Example 4), prompted the investigation of the effects of introducing a transforming factor (such as TGF-β) in an encapsulated form (e.g., liposomes) from which the transforming factor would be released when the matrix was completely populated with repair cells that had begun to remodel the intercellular structure.

TGF-β was mixed into the fibrinogen solution (1 mg/ml) at a low concentration (e.g., 2–10 ng/ml) for the purpose of promoting the initial chemotactic and proliferative effects. TGF-β was also encapsulated in liposomes according to the method of Kim et al. (1983) supra. These TGF-β containing liposomes were added to the same fibrinogen solution in a concentration adequate to provide, when the liposomes were ruptured and the TGF-β was released, the higher concentration of 100–1000 ng of TGF-β per ml of fibrinogen for the purpose of promoting transformation of the repair cells into chondrocytes and transformation of the matrix-filled defect into cartilage during a secondary stage when the repair cells populating the fibrin matrix have begun to remodel the intercellular substance.

Ten mature rabbits, in which superficial knee joint articular cartilage defects were produced as in Example 2, were treated by application of this mixture of fibrinogen containing free and liposome-encapsulated TGF-β to the defect site. In the various experiments in this series of experiments, the concentration of free TGF-β was maintained in the range from 2–10 ng/ml of fibrinogen while the concentration of encapsulated TGF-β was varied to provide (upon release of the TGF-β from the liposomes) a concentration between 100 and 1000 ng TGF-β/ml fibrinogen in 100 ng steps. Formation of hyaline cartilage tissue occurred at the treatment sites in all cases. The most reproducible results were obtained at concentrations of above 200 ng encapsulated TGF-β/ml fibrinogen solution, and preferably above 500 ng TGF-β/ml of fibrinogen solution.

EXAMPLE 6

Determination of the Time Point of Tissue Transformation

In this experiment, a group of six mature rabbits were subjected to knee surgery to produce superficial defects as in Example 2. A full treatment scheme for superficial defect repair was applied, i.e., treatment with chondroitinase ABC (1 U/ml for 4 minutes), followed by filling the defect site with fibrin matrix (1 mg/ml fibrinogen solution, 20 μl 100 U/ml thrombin solution per ml of fibrinogen solution) containing free TGF-β (~2–10 ng/ml) and liposome encapsulated TGF-β (~800 ng/ml). Three rabbits were sacrificed at eight, ten and twelve days postoperatively, the remaining three at twenty, twenty-four and twenty-eight days. Transformation of the primitive, fibroblast-like repair cell tissue into hyaline cartilage tissue occurred between days twelve and twenty in this animal model. This was determined on the basis of histological examination. At days eight to twelve, loose fibrous repair tissue was still present (the applied fibrin matrix being partially or completely remodeled), whereas at day twenty and subsequently, the defect space was partially or completely filled with hyaline cartilage tissue.

EXAMPLE 7

Application of Cartilage Repair Procedures in a Mini-pig Model

The experimental procedures utilized in the rabbit model, supra, were applied to a larger animal model, the mini-pig. Superficial defects (0.6 mm wide, 0.6 mm deep and approximately 10–15 mm long) were created in four mature mini-pigs (2–4 years old, 80–110 lbs.) by cutting with a planing knife in the patellar groove and on the medial condyle. The defects were then treated with chondroitinase ABC (1 U/ml for 4 minutes, as used for rabbits, supra). The enzyme solution was removed, the defect dried, rinsed with physiological saline, then dried again. The defect sites were then filled with a fibrinogen matrix solution. The fibrinogen matrix solution used in this experiment contained 2–6 ng of free TGF-β per ml, and 1500–2000 ng of liposome-encapsulated TGF-β per ml of fibrinogen solution. Prior to filling the defects, thrombin was added to the matrix solution as described above in the rabbit experiment.

The mini-pigs were sacrificed 6 weeks postoperatively, and the sites of the matrix-filled defects were examined histologically. All sites showed healing, i.e., formation of hyaline cartilage tissue at the treatment site.

EXAMPLE 8

Repair of Full-Thickness Defects in Articular Cartilage Using Anti-Angiogenic Agent Full-thickness articular cartilage defects, 1 mm deep and 10 mm wide, were created in the medial condyles and patellar grooves of adult mini-pig knee joints. Five lesions were effected in each of two animals, using a planing instrument. In each patellar groove, two defects were made in the cranial region, two defects in the caudal region and one defect in the medial femoral condyle. The vertical extensions of each lesion into the subchondral bone (containing blood vessels and bone marrow cells) was controlled macroscopically by the occurrence of bleeding to insure that a full-thickness lesion had been made in the joint. The defects were then treated with chondroitinase AC (1 U/ml for 4 minutes). The enzyme solution was removed, the defect dried, rinsed with physiological saline, then dried again. The defect sites were then filled with a cartilage repair matrix solution. The matrix solution used in this experiment consisted of a copolymer of gelatin (Gelfoam, Upjohn) (used at 100 mg per ml) and fibrinogen (used at 20 mg per ml). Thrombin (used at 50 I.U.) was added to the top surface of the defect after the matrix was placed in the defect and was allowed to diffuse into the matrix.

The cartilage repair matrix contained a free proliferation agent insulin-like growth factor-1 (IGF-1) at a concentration of about 40 ng/ml of matrix volume as a transforming factor, and liposome-encapsulated TGF-β1 at a concentration of 500 ng/ml of matrix volume as a transforming factor. In addition, free Suramin was added at a concentration of 10 millimolar of matrix volume and liposome-encapsulated Suramin was added at a concentration of 10 millimolar of matrix volume in the same liposomes that contained the TGF-β1. In control lesions, defects were treated in the same manner, except that Suramin was not added.

About 8 weeks after the operation and treatment, the animals were sacrificed and the sites of the matrix-filled defects examined histologically. The part of the defect space adjacent to articular cartilage tissue, i.e., in the region filled with the matrix composition containing Suramin, was filled with articular cartilage tissue. The same part of the defect space in control lesions, i.e., those treated without Suramin, was filled with newly-formed bone tissue.

The above experiment was repeated with the substitution of BMP-2 for TGF-β1, at a concentration of 1000 ng/ml of matrix volume. The same results were obtained.

EXAMPLE 9

Repair of Full-Thickness Defects in Articular Cartilage Using Heating Procedure Full-thickness articular cartilage defects, 1 mm deep and 10 mm wide, were created in the medial condyles and patellar grooves of adult mini-pigs. Five lesions were effected in each knee joint of two mini-pigs. At each location where bleeding occurred, coagulation was induced by applying a heated instrument to the floor of defects to form a biological physical barrier. We used a heated scalpel blade (heated to 220° C.) to create the transient tissue barrier.

In one mini-pig, articular cartilage defects in one joint were filled with a cartilage repair matrix containing IGF-1 at a concentration of about 40 ng/ml of matrix volume and liposome-encapsulated TGF-β3 at a concentration of 500 ng/ml of matrix volume. In the defect in the other joint, Suramin was included in the matrix as described in Example 8.

In the second mini-pig, the defects of one joint were filled with a cartilage repair matrix containing IGF-1 at a concentration of about 40 ng/ml of matrix volume and liposome-encapsulated BMP-2 at a concentration of 1000 ng/ml of matrix volume. In the defects of the other joint of the second mini-pig, Suramin was included in the matrix as described in Example 8.

As in the previous experiment, the animals were sacrificed and examined eight weeks after operation and treatment. No bone tissue formed in the defect space adjacent to articular cartilage tissue in either animal. Rather, the defect spaces were filled with articular cartilage tissue.

EXAMPLE 10

Repair of Deep Full-Thickness Defects in Articular Cartilage Using Anti-Angiogenic Agent Very deep full-thickness articular cartilage defects, up to 5 mm deep, can be created in the medial condyles and patellar grooves of adult mini-pig knee joints. Lesions can be effected in animals maintained under general anaesthesia, using a planing instrument. The bone portion of the defect may be filled with a bone repair matrix composition such as those described above. The bone portion of the defect should be filled with matrix up to the cartilage-bone interface. The articular cartilage defect space can be filled with a cartilage repair matrix containing an anti-angiogenic factor, such as those described above, e.g., at Examples 8–9.

I claim:

1. A method for treating full-thickness defects in cartilage in animals which comprises:
   filling the cartilage portion of the defect with a matrix containing an effective amount of an anti-angiogenic agent to prevent ingrowth of blood vessels into the cartilage.

2. The method of claim 1 wherein the matrix further contains an effective amount of a transforming factor to transform repair cells into chondrocytes.

3. The method of claim 2 wherein the matrix further contains an effective amount of a proliferation agent to stimulate proliferation of repair cells.

4. The method of claim 3 wherein the matrix further contains an effective amount of a chemotactic agent to attract repair cells.

5. The method of claims 2 or 3 wherein the transforming factor is associated with a delivery system that releases the transforming factor at a concentration sufficient to transform repair cells into chondrocytes.

6. The method of claim 5 wherein the anti-angiogenic agent is contained in the matrix both in free form and associated with a delivery system to provide sustained release.

7. The method of claim 1 further comprising delivering an effective amount of a transforming factor to the matrix-filled defect at a time when repair cells have populated the matrix to transform the repair cells into chondrocytes.

8. A method for treating full-thickness defects in cartilage in animals which comprises:
   heat treating locations of bleeding to create a transient biological membrane; and
   filling the cartilage portion of the full-thickness defect with a matrix containing an effective amount of a proliferation agent to stimulate proliferation of repair cells and an effective amount of a transforming factor associated with a delivery system that releases the transforming factor at a concentration sufficient to transform repair cells into chondrocytes.

9. The method of claim 8 wherein the matrix further contains an effective amount of an anti-angiogenic agent to prevent ingrowth of blood vessels into the cartilage.

10. The method of claim 8 wherein the matrix further contains an effective amount of a chemotactic agent to attract repair cells.

11. The method of claim 2 further comprising filling the bone portion of the defect with a second matrix.

12. The method of claim 11 wherein the second matrix contains an effective amount of an angiogenic factor to stimulate formation and ingrowth of blood vessels with associated cells and containing an osteogenic factor associated with a delivery system that releases the osteogenic factor at a concentration sufficient to induce differentiation of bone repair cells into bone cells which form bone.

13. A method of treating defects in cartilage in animals which comprises:
   filling the defect with a matrix containing an effective amount of anti-angiogenic agent to prevent ingrowth of blood vessels into the cartilage, an effective amount of a chemotactic agent to attract repair cells, an effective amount of a proliferation agent to stimulate proliferation of repair cells, and an effective amount of a transforming factor associated with a delivery system that releases the transforming factor at a concentration sufficient to transform repair cells into chondrocytes.

14. The method of claim 13 wherein the anti-angiogenic agent is contained in the matrix both in free form and associated with a delivery system to provide sustained release.

15. The method of claims 1, 8 or 11 further comprising treating the defect site with a sterile solution of an agent to degrade proteogylcans from the surface of the defect and removing the agent prior to filling the defect with the matrix.

16. The method of claim 15 wherein the agent to degrade proteoglycans is chondroitinase AC.

17. The method of claim 6 wherein the delivery system is selected from the group consisting of liposomes, bioerodible polymers, collagen fibers, carbohydrate-based corpuscles, and water-oil emulsions.

18. The method of claim 17 wherein the matrix is selected from the group consisting of fibrin, collagen, gelatin, agarose, and combinations thereof.

19. The method of claim 11 wherein the matrix used to fill the cartilage portion of the defect is selected from the group consisting of fibrin, collagen, gelatin, agarose, and combinations thereof, and the second matrix used to fill the bone portion of the defect is selected from the group consisting of matrices containing calcium salts.

20. The method of claim 2 wherein the anti-angiogenic agent is suramin.

21. The method of claim 2 wherein the transforming factor is selected from the group consisting of TGF-β and BMP.

22. The method of claim 12 wherein the transforming factor is selected from the group consisting of TGF-β and BMP, and the osteogenic factor is selected from the group consisting of TGF-β, BMP and FGF.

23. A composition for the treatment of defects in cartilage comprising:
- a biodegradable matrix or matrix-forming material used to dress the area of the defect or lesion in the cartilage;
- an effective amount of an anti-angiogenic agent to prevent ingrowth of blood vessels into the cartilage; and
- an effective amount of one or more agents selected from the group consisting of a transforming factor to transform repair cells into chondrocytes, a proliferation agent to stimulate proliferation of repair cells, and a chemotactic agent to attract repair cells.

24. The composition of claim 23 wherein the transforming factor is associated with a delivery system.

25. The composition of claim 24 wherein the anti-angiogenic agent is in free form and is also associated with a delivery system.

26. The composition of claim 25 wherein the transforming factor and the anti-angiogenic agent are associated with the same delivery system.

27. The composition of claim 26 in which the delivery system for the delivery of the transforming factor and the anti-angiogenic agent is selected from the group consisting of liposomes, bioerodible polymers, collagen fibers, carbohydrate-based corpuscles, and water-oil emulsions.

28. The composition of claim 23 wherein the matrix is selected from the group consisting of fibrin, collagen, gelatin, agarose, and combinations thereof.

29. The composition of claim 25 wherein the anti-angiogenic agent is suramin.

30. The composition of claim 24 wherein the transforming factor is selected from the group consisting of TGF-β and BMP.

* * * * *